United States Patent
Bai (10) Patent No.: US 10,719,695 B2
(45) Date of Patent: Jul. 21, 2020

(54) METHOD FOR PUSHING PICTURE, MOBILE TERMINAL, AND STORAGE MEDIUM

(71) Applicant: Guangdong Oppo Mobile Telecommunications Corp., Ltd., Dongguan, Guangdong (CN)

(72) Inventor: Jian Bai, Guangdong (CN)

(73) Assignee: GUANGDONG OPPO MOBILE TELECOMMUNICATIONS CORP., LTD., Dongguan (CN)

( * ) Notice: Subject to any disclaimer, the term of this patent is extended or adjusted under 35 U.S.C. 154(b) by 294 days.

(21) Appl. No.: 15/957,360

(22) Filed: Apr. 19, 2018

(65) Prior Publication Data

US 2018/0349686 A1 Dec. 6, 2018

(30) Foreign Application Priority Data

May 31, 2017 (CN) .......................... 2017 1 0401789

(51) Int. Cl.
*G06K 9/62* (2006.01)
*G06K 9/00* (2006.01)
*A61B 5/16* (2006.01)
*G06F 3/01* (2006.01)
*A61B 5/00* (2006.01)

(52) U.S. Cl.
CPC ........ *G06K 9/00302* (2013.01); *A61B 5/0077* (2013.01); *A61B 5/165* (2013.01); *A61B 5/6898* (2013.01); *A61B 5/7264* (2013.01); *G06F 3/011* (2013.01); *G06K 9/6256* (2013.01); *G06F 2203/011* (2013.01)

(58) Field of Classification Search
CPC .. H04N 19/176; H04N 19/124; H04N 19/597; H04N 19/115; H04N 19/14; G06K 9/00302; A63F 13/213; A63F 13/216; A63F 13/35; A63F 13/65
USPC .......................... 382/155; 434/262; 455/418
See application file for complete search history.

(56) References Cited

U.S. PATENT DOCUMENTS

| | | | |
|---|---|---|---|
| 6,931,147 B2 | 8/2005 | Colmenarez et al. | |
| 8,704,760 B2 | 4/2014 | Kang et al. | |
| 10,387,717 B2 * | 8/2019 | Li | ...................... G06K 9/00664 |
| 2010/0321519 A1 | 12/2010 | Bill | |
| 2015/0235366 A1 | 8/2015 | Lee et al. | |

FOREIGN PATENT DOCUMENTS

| | | |
|---|---|---|
| CN | 1940806 A | 4/2007 |
| CN | 101958971 A | 1/2011 |
| CN | 102300163 A | 12/2011 |
| CN | 102479024 A | 5/2012 |

(Continued)

OTHER PUBLICATIONS

Extended European search report issued in corresponding European application No. 18166575.3 dated Oct. 2, 2018.

(Continued)

*Primary Examiner* — Charlotte M Baker (57) ABSTRACT

Provided are a method for pushing a picture, a terminal and a storage medium. The method includes the follows. An image containing a facial expression of a user is acquired, when a screen is lit; the image is analyzed to determine an emotion type of the user; and a target picture is pushed according to the emotion type of the user.

8 Claims, 7 Drawing Sheets

(56) References Cited

FOREIGN PATENT DOCUMENTS

| | | | |
|---|---|---|---|
| CN | 102929660 A | 2/2013 |
| CN | 104202718 A | 12/2014 |
| CN | 105534534 A | 5/2016 |
| CN | 105956059 A | 9/2016 |
| CN | 106126017 A | 11/2016 |
| CN | 106708394 A | 5/2017 |

OTHER PUBLICATIONS

Search report issued in corresponding SG application No. 11201905655W dated Apr. 28, 2020.

\* cited by examiner

METHOD FOR PUSHING PICTURE, MOBILE TERMINAL, AND STORAGE MEDIUM

CROSS-REFERENCE TO RELATED APPLICATION(S)

This application claims priority to Chinese patent application no. 201710401789.5, filed on May 31, 2017, the contents of which is herein incorporated by reference in its entirety.

TECHNICAL FIELD

The present disclosure relates to the field of terminals, and particularly to a method for pushing a picture, a mobile terminal, and a storage medium.

BACKGROUND

At present, with the development of science technology, the material life of people is brought to be greatly enriched, and smart terminals also become popular.

People can work, entertain, and play games through a smart terminal. Specifically, a server may push pictures to a terminal periodically; however, the pushed pictures are not likely to be applied as wallpapers of the terminal by a user since the server does not know a state of the user. Additionally, it is hard for the user to choose a favorite picture from the pushed pictures and generally, the user will open a webpage to choose a picture that fits his or her style, the whole process of choosing the picture on the webpage may take a lot of time, which is inconvenient to the user.

SUMMARY

Implementations of the present disclosure disclose a method for pushing a picture, a mobile terminal, and a storage medium, which can push a target picture which matches with an emotion type of a user, so as to push a favorite picture of the user more likely, and then, the time for the user choosing the picture is reduced.

A first aspect of an implementation of the present disclosure discloses a method for pushing a picture, which includes the follows.

An image containing a facial expression of a user is acquired, when a screen is lit; the image is analyzed to determine an emotion type of the user; and a target picture is pushed according to the emotion type of the user.

A second aspect of the present disclosure discloses a mobile terminal, which includes a memory configured to store program codes and at least one processor coupled with the memory, wherein the program codes, when executed by the at least one processor, is operable with the at least one processor to perform: an acquiring unit, an analyzing unit, a determining unit, an obtaining unit, and a pushing unit. The acquiring unit is configured to acquire an image containing a facial expression of a user, when a screen is lit. The analyzing unit is configured to analyze the image to determine an emotion type of the user. The determining unit is configured to determine a type of a picture to be pushed according to the emotion type of the user. The obtaining unit is configured to obtain a target picture that matches with the type of the picture to be pushed from a picture gallery. The pushing unit is configured to push the target picture to the user.

A third aspect of the present disclosure discloses a mobile terminal, which includes a camera and a general-purpose processor. The camera is configured to acquire an image containing a facial expression of a user, when a screen is lit. The general-purpose processor is configured to: analyze the image to determine an emotion type of the user; determine a type of a picture to be pushed according to the emotion type of the user; obtain a target picture that matches with the type of the picture to be pushed from a picture gallery; and push the target picture to the user.

BRIEF DESCRIPTION OF THE DRAWINGS

To describe the technical solutions in the implementations of the present disclosure more clearly, the following briefly introduces the accompanying drawings required for describing the implementations. Apparently, the accompanying drawings in the following description show some implementations of the present disclosure. Those of ordinary skill in the art may also obtain other drawings based on these accompanying drawings without creative efforts.

DETAILED DESCRIPTION

Technical solutions in the implementations of the present disclosure will be described clearly and completely hereinafter with reference to the accompanying drawings in the implementations of the present disclosure. Apparently, the described implementations are merely some rather than all implementations of the present disclosure. All other implementations obtained by those of ordinary skill in the art based on the implementations of the present disclosure without creative efforts shall fall within the protection scope of the present disclosure.

There is provided a method for pushing a picture, a mobile terminal, and a storage medium according to implementations of the present disclosure, which can push a target picture that matches with an emotion type of a user, so as to push a favorite picture of the user more likely and reduce the time the user chooses the picture. Implementations of the present disclosure will be described in detail in following.

According to implementations of the disclosure, there is provided a method for pushing a picture, which includes the following.

An image containing a facial expression of a user is acquired, when a screen is lit; the image is analyzed to determine an emotion type of the user; and a target picture is pushed according to the emotion type of the user.

As one implementation, the target picture is pushed according to the emotion type of the user as follows. A type of a picture to be pushed is determined according to the emotion type of the user; the target picture that matches with the type of the picture to be pushed is obtained from a picture gallery; and the target picture is pushed to the user.

As one implementation, the image is analyzed to determine an emotion type of the user as follows. The image is compared with a template to determine a location of eyes and a location of mouth; a shape of the eyes and a shape of the mouth are analyzed to determine the emotion type of the user.

As one implementation, the image is analyzed to determine an emotion type of the user as follows. The image is compared with a template to determine locations of multiple facial features; shapes of the facial features are analyzed to determine multiple candidate emotion types; and an emotion type with the highest proportion among the candidate emotion types is determined as the emotion type of the user.

As one implementation, the image is analyzed to determine an emotion type of the user as follows. The image is compared with a user emotion model to determine a target emotion picture from the user emotion model that matches with the image; and the emotion type of the user is determined according to the target emotion picture.

As one implementation, the method may further include the following before comparing the image with the user emotion model to determine the target emotion picture from the user emotion model that matches with the image. A preset number of expression images of the user are acquired; and the expression images are learned according to a preset machine learning scheme to obtain the user emotion model.

As one implementation, the method may further include the following after pushing the target picture to the user. A choosing result of the user is recorded; and the user emotion model is updated according to the choosing result of the user.

According to implementations of the disclosure, there is provided a mobile terminal, which includes a memory configured to store program codes and at least one processor coupled with the memory, wherein the program codes, when executed by the at least one processor, is operable with the at least one processor to perform the following.

An acquiring unit configured to acquire an image containing a facial expression of a user, when a screen is lit; an analyzing unit configured to analyze the image to determine an emotion type of the user; a determining unit configured to determine a type of a picture to be pushed according to the emotion type of the user; an obtaining unit configured to filter a picture gallery to obtain a target picture that matches with the type of the picture to be pushed; a pushing unit configured to push the target picture to the user.

As one implementation, the analyzing unit includes a first comparing unit and an analyzing unit.

The first comparing unit is configured to compare the image with a template to determine a location of eyes and a location of mouth.

The analyzing unit is configured to analyze a shape of the eyes and a shape of the mouth to determine the emotion type of the user.

As one implementation, the analyzing unit includes a third comparing unit, a first determining unit, and a second determining unit.

The third comparing unit is configured to compare the image with a template to determine locations of multiple facial features.

The first determining unit is configured to analyze shapes of the facial features to determine multiple candidate emotion types.

The second determining unit is configured to determine an emotion type with the highest proportion among the candidate emotion types as the emotion type of the user.

As one implementation, the analyzing unit includes a second comparing unit and a determining unit.

The second comparing unit is configured to compare the image with a user emotion model to determine a target emotion picture from the user emotion model that matches with the image.

The determining unit is configured to determine the emotion type of the user according to the target emotion picture.

As one implementation, the mobile terminal may further include a learning unit.

The acquiring unit is further configured to acquire a preset number of expression images of the user.

The learning unit is configured to learn the expression images according to a preset machine learning scheme to obtain the user emotion model.

As one implementation, the mobile terminal may further include a recording unit and an updating unit.

The recording unit is configured to record a choosing result of the user.

The updating unit is configured to update the user emotion model according to the choosing result of the user.

According to the implementations of the disclosure, there is provided another mobile terminal, which includes a camera and a general-purpose processor.

The camera is configured to acquire an image containing a facial expression of a user, when a screen is lit.

The general-purpose processor is configured to: analyze the image to determine an emotion type of the user; determine a type of a picture to be pushed according to the emotion type of the user; filter a picture gallery to obtain a target picture that matches with the type of the picture to be pushed; and push the target picture to the user.

As one implementation, the general-purpose processor configured to analyze the image to determine an emotion type of the user is configured to: compare the image with a template to determine a location of eyes and a location of mouth, and analyze a shape of the eyes and a shape of the mouth to determine the emotion type of the user.

As one implementation, the general-purpose processor configured to analyze the image to determine an emotion type of the user is configured to: compare the image with a user emotion model to determine a target emotion picture from the user emotion model that matches with the image and determine the emotion type of the user according to the target emotion picture.

As one implementation, the general-purpose processor is further configured to: acquire a preset number of expression images of the user and learn the expression images according to a preset machine learning scheme to obtain the user emotion model.

As one implementation, the general-purpose processor includes an application processor and an artificial intelligence (AI) unit, and the AI unit is integrated with the application processor.

The AI unit is configured to acquire a preset number of expression images of the user and learn the expression images according to a preset machine learning scheme to obtain the user emotion model.

As one implementation, the AI unit is further configured to compare the image with the user emotion model to determine the target emotion picture from the user emotion model that matches with the image and determine the emotion type of the user according to the target emotion picture.

As one implementation, the general-purpose processor includes an application processor and an artificial intelligence (AI) unit, the AI unit is separated from the application processor.

The AI unit is configured to acquire a preset number of expression images of the user and learn the expression images according to a preset machine learning scheme to obtain the user emotion model.

As one implementation, the AI unit is further configured to compare the image with the user emotion model to determine the target emotion picture from the user emotion model that matches with the image and determine the emotion type of the user according to the target emotion picture.

First Implementation

Figure 1A:
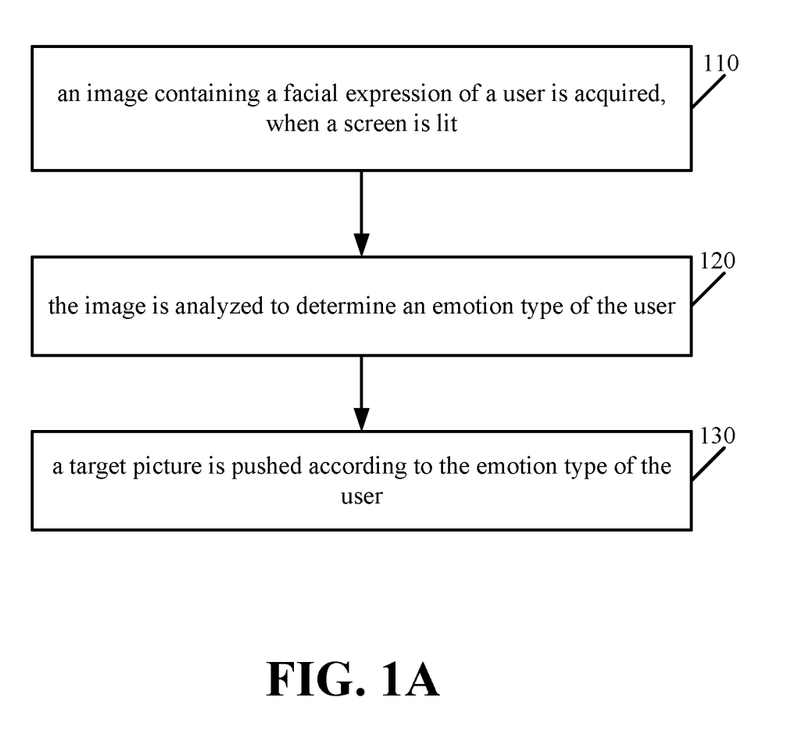
FIG. 1A is a schematic flowchart illustrating a method for pushing a picture according to an implementation of the present disclosure.

FIG. 1A is a schematic flowchart illustrating a method for pushing a picture according to a first implementation of the disclosure. This implementation can be applied to a situation where a user wants to change a wallpaper of a terminal, so the method can be performed by a terminal with a display screen. The terminal can be an electronic terminal such as a smart phone and a tablet PC. As illustrated in FIG. 1A, the method begins at block 110.

At block 110, an image containing a facial expression of a user is acquired, when a screen is lit.

In at least one implementation of the present disclosure, the terminal may include various types of terminals such as a mobile phone, a tablet computer, a personal digital assistant (PDA), and a mobile Internet device (MID), the implementations of the present disclosure is not limited thereto.

It should be noted that, the image shows the user's eyes, nose, cheeks, lips, eyebrows, and the like.

When this method is performed by a terminal, the image is acquired when a screen of the terminal is lit.

At block 120, the image is analyzed to determine an emotion type of the user.

Emotion types are classifications of the emotion of a user. A common emotion type includes good mood, normal mood, or bad mood.

It should be noted that, the image can be analyzed partially to determine the emotion type of the user (such as only analyzing the shape of the eyes and mouth), and the image can also be analyzed entirely to determine the emotion type of the user (such as comparing the image with a model directly to determine the emotion type of the user).

At block 130, a target picture is pushed according to the emotion type of the user.

The terminal can determine the target picture according to the emotion type of the user, and push the target picture to the user.

Through the above technical solution, the target picture which matches with the emotion type of the user can be pushed, so as to push a favorite picture of the user more likely and reduce the time for the user choosing the picture.

Second Implementation

Figure 1B:
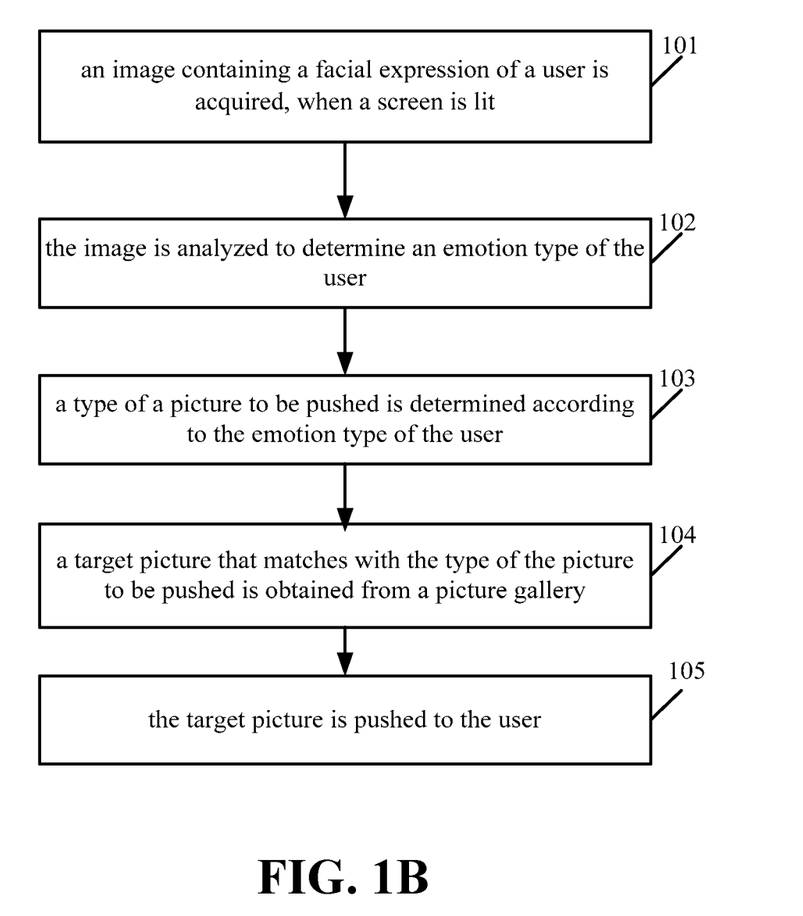
FIG. 1B is a schematic flowchart illustrating a method for pushing a picture according to an implementation of the present disclosure.

FIG. 1B is a schematic flowchart illustrating a method for pushing a picture according to a second implementation of the disclosure. This implementation can be applied to a situation where a user wants to change a wallpaper of a terminal, so the method can be performed by a terminal with a display screen. The terminal can be an electronic terminal such as a smart phone and a tablet PC. As illustrated in FIG. 1B, the method begins at block 101.

At block 101, an image containing a facial expression of a user is acquired, when a screen is lit.

In at least one implementation of the present disclosure, the terminal may include various types of terminals such as a mobile phone, a tablet computer, a personal digital assistant (PDA), and a mobile internet device (MID), the implementations of the present disclosure is not limited thereto.

It should be noted that, the image shows the user's eyes, nose, cheeks, lips, eyebrows, and the like.

When this method is performed by a terminal, the image is acquired when a screen of the terminal is lit.

At block 102, the image is analyzed to determine an emotion type of the user.

Emotion types are classifications of the emotion of a user. A common emotion type includes good mood, normal mood, or bad mood.

It should be noted that, the image can be analyzed partially to determine the emotion type of the user (such as only analyzing the shape of the eyes and mouth), and the image can also be analyzed entirely to determine the emotion type of the user (such as comparing the image with a model directly to determine the emotion type of the user).

As an implementation, the image is analyzed as follows to determine the emotion type of the user: the image is compared with a template to determine a location of eyes and a location of mouth; and a shape of the eyes and a shape of the mouth are analyzed to determine the emotion type of the user.

For instance, the template includes a division of facial features of human face, facial features contained in the image are marked by comparing the image with the template, such as marking out where is the mouth, where are the eyes, where are the eyebrows, and where are the cheeks, etc.

The shape of the eyes is analyzed as follows: the shape of the eyes is compared with preset eye shapes to determine the emotion type of the user. It could be understood that, the preset eye shapes are all marked, for example, a preset eye shape of bent is marked as a good mood. If the shape of the eyes matches with the bent eye shape, it indicates that the user is in good mood.

The shape of the mouth is analyzed as follows: the shape of the mouth is compared with preset mouth shapes to determine the emotion type of the user.

It could be understood that, a mouth shape with upturned angulus oris will be generally marked as a good mood. If the shape of the mouth matches with the mouth shape with upturned angulus oris, it indicates that the user is in good mood. If the mouth shape is that lips close tightly, it indicates that the user is in general mood or in bad mood.

It could be understood that, if an analysis result of the shape of the eyes is different from an analysis result of the mouth, a shape(s) of the eyebrows can further be analyzed to acquire an analysis result. Proportions of analysis results are counted. After analyzing multiple parts, if more than a half parts indicate that the user is in good mood, a final result to be output is that the user is in good mood.

As an implementation, the image is analyzed as follows to determine the emotion type of the user: the image is compared with a user emotion model to determine a target emotion picture from the user emotion model that matches with the image; and the emotion type of the user is determined according to the target emotion picture.

It should be pointed out that, the user emotion model includes multiple face images, and each face image has been marked with an emotion type. If a matching rate between the image and a first image is greater than a preset threshold (such as 95%), the emotion type corresponding to the first image is the emotion type of the user. The first image is any image in the user emotion model.

In addition, before the image is compared with the user emotion model to determine the target emotion picture from the user emotion model that matches with the image, the method further includes: a preset number of expression images of the user are acquired; the expression images are learned according to a preset machine learning scheme to obtain the user emotion model.

For instance, a terminal can acquire images containing a facial expression of the user from a picture gallery of the terminal, then the terminal sends a part of the images to a server to cause the server to mark the received images with emotion type; the terminal receives marked images from the server, and learns the remaining acquired images according to the marked images and the preset machine learning scheme to obtain the user emotion model. It could be understood that, the user emotion model could be a user picture gallery, and all images in the user picture gallery are marked with an emotion type.

Common preset learning schemes include classification algorithm, supervised learning algorithm, Bayesian algorithm, etc., just to name a few.

At block 103, a type of a picture to be pushed is determined according to the emotion type of the user.

For instance, if the emotion type of the user is that the user is in good mood, the pictures to be pushed can be outdoor scenery pictures. If the emotion type of the user is that the user is in bad mood, the pictures to be pushed can be funny pictures or humorous pictures.

At block 104, a target picture that matches with the type of the picture to be pushed is obtained from a picture gallery.

Pictures stored in the terminal can be filtered. The terminal can certainly send a picture acquiring request to a cloud data center, and the picture acquiring request contains a picture type; the cloud data center searches the Internet to acquire pictures belonging to the picture type, and returns the pictures acquired to the terminal; after receiving the pictures returned by the cloud data center, the terminal can pop up a thumbnail on the desktop for the user to browse, so as to provide the user with convenience to choose a picture.

At block 105, the target picture is pushed to the user.

As an implementation, after the target picture is pushed to the user, the method further includes: a choosing result of the user is recorded; the user emotion model is updated according to the choosing result of the user.

It can be seen from the above that by implementing the technical solutions provided by the implementations of the present disclosure, an image containing a facial expression of a user is acquired, when a screen is lit; the image is analyzed to determine an emotion type of the user; a type of a picture to be pushed is determined according to the emotion type of the user; a picture gallery is filtered to obtain a target picture that matches with the type of the picture to be pushed; and the target picture is pushed to the user. Through the above technical solution, the target picture which matches with the emotion type of the user can be pushed, so as to push a favorite picture of the user more likely and reduce the time for the user choosing the picture.

Third Implementation

The third implementation provides a method for pushing a picture on the basis of the second implementation. In this method, an image containing a facial expression of a user is analyzed partially to determine an emotion type of the user as follows. The image is compared with a template to determine a location of eyes and a location of mouth; and a shape of the eyes and a shape of the mouth are analyzed to determine the emotion type of the user.

Figure 2:
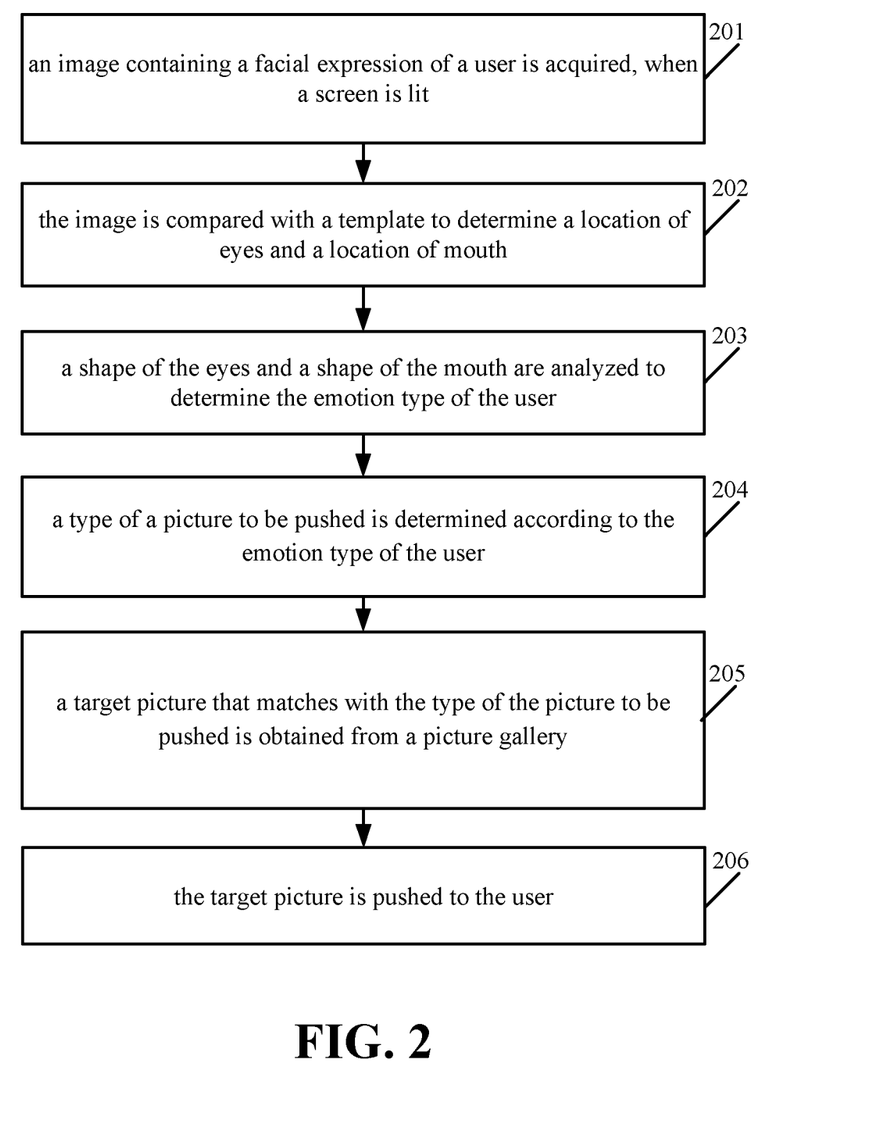
FIG. 2 is a schematic flowchart illustrating another method for pushing a picture according to an implementation of the present disclosure.

Referring to FIG. 2, FIG. 2 is a schematic flowchart illustrating a method for pushing a picture according to an implementation of the present disclosure. As shown in FIG. 2, the method for pushing a picture begins at block 201.

At block 201, an image containing a facial expression of a user is acquired, when a screen is lit.

In at least one implementation of the present disclosure, the terminal may include various types of terminals such as a mobile phone, a tablet computer, a personal digital assistant (PDA), and a mobile internet device (MID), the implementations of the present disclosure is not limited thereto.

At block 202, the image is compared with a template to determine a location of eyes and a location of mouth.

At block 203, a shape of the eyes and a shape of the mouth are analyzed to determine the emotion type of the user.

A common emotion type includes good mood, normal mood, or bad mood.

For instance, the template includes a division of facial features of human face, facial features contained in the image are marked by comparing the image with the template, such as marking out where is the mouth, where are the eyes, where are the eyebrows, and where are the cheeks, etc.

The shape of the eyes is analyzed as follows: the shape of the eyes is compared with preset eye shapes to determine the emotion type of the user. It could be understood that, the preset eye shapes are all marked, for example, a preset eye shape of bent is marked as a good mood. If the shape of the eyes matches with the bent eye shape, it indicates that the user is in good mood.

The shape of the mouth is analyzed as follows: the shape of the mouth is compared with preset mouth shapes to determine the emotion type of the user.

It could be understood that, a mouth shape with upturned angulus oris will be generally marked as a good mood. If the shape of the mouth matches with the mouth shape with upturned angulus oris, it indicates that the user is in good mood. If the mouth shape is that lips close tightly, it indicates that the user is in general mood or in bad mood.

It could be understood that, if an analysis result of the shape of the eyes is different from an analysis result of the mouth, a shape(s) of the eyebrows can further be analyzed to acquire an analysis result. Proportions of analysis results are counted. After analyzing multiple parts, if more than a half parts indicate that the user is in good mood, a final result to be output is that the user is in good mood.

At block 204, a type of a picture to be pushed is determined according to the emotion type of the user.

For instance, if the emotion type of the user is that the user is in good mood, the pictures to be pushed can be outdoor scenery pictures. If the emotion type of the user is that the user is in bad mood, the pictures to be pushed can be funny pictures or humorous pictures.

At block 205, a target picture that matches with the type of the picture to be pushed is obtained from a picture gallery.

Thereinto, pictures stored in the terminal can be filtered. The terminal can certainly send a picture acquiring request to a cloud data center, and the picture acquiring request contains a picture type; the cloud data center searches the Internet to acquire pictures belonging to the picture type, and returns the pictures acquired to the terminal; after receiving the pictures returned by the cloud data center, the terminal can pop up a thumbnail on the desktop for the user to browse, so as to provide the user with convenience to choose a picture.

At block 206, the target picture is pushed to the user.

In the method described in FIG. 2, the image is compared with the template to determine the location of eyes and the location of mouth; the shape of the eyes and the shape of the mouth are analyzed to determine the emotion type of the user. By analyzing the image containing facial features partially to determine the emotion type of the user and recommending a picture matching with the emotion type of the user, it is convenient for the user to acquire a picture matching the current mood.

Fourth Implementation

The fourth implementation provides a method for pushing a picture on the basis of the second implementation. In this method, an image containing a facial expression of a user is analyzed entirely to determine an emotion type of the user as follows. The image is compared with a user emotion model to determine a target emotion picture from the user emotion model that matches with the image; and the emotion type of the user is determined according to the target emotion picture.

Figure 3:
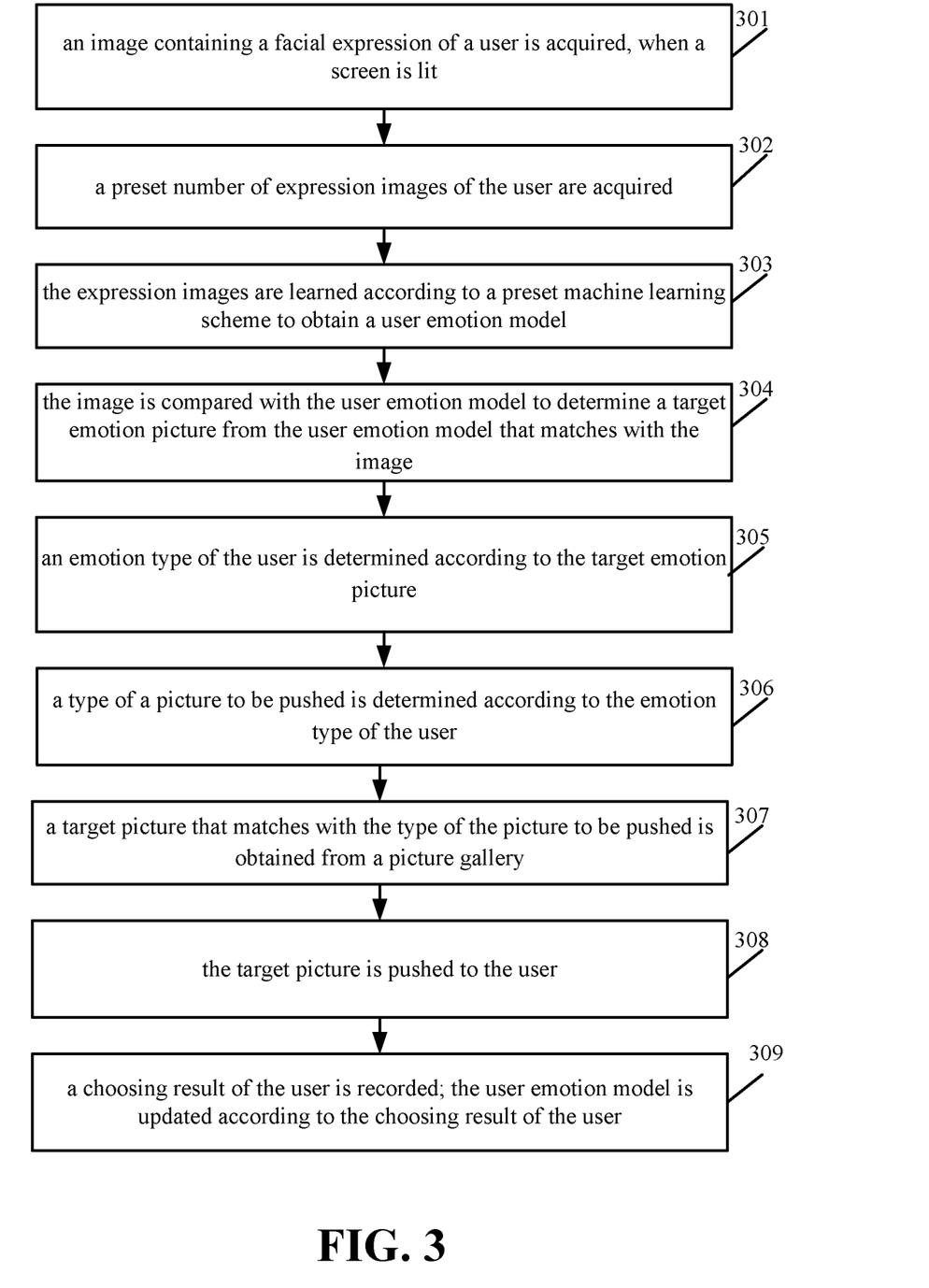
FIG. 3 is a schematic flowchart illustrating another method for pushing a picture according to an implementation of the present disclosure.

Referring to FIG. 3, FIG. 3 is a schematic flowchart illustrating a method for pushing a picture disclosed by an implementation of the present disclosure. As shown in FIG. 3, the method for pushing a picture begins at block 301.

At block 301, an image containing a facial expression of a user is acquired, when a screen is lit.

At block 302, a preset number of expression images of the user are acquired.

At block 303, the expression images are learned according to a preset machine learning scheme to obtain a user emotion model.

Common preset learning schemes include classification algorithm, supervised learning algorithm, Bayesian algorithm, etc., just to name a few.

For instance, a terminal can acquire images containing a facial expression of the user from a picture gallery of the terminal, then the terminal sends a part of images to a server to cause the server to mark the received images with emotion type; the terminal receives marked images from the server, and learns the remaining acquired images according to the marked images and the preset machine learning scheme to obtain the user emotion model. It could be understood that, the user emotion model could be a user picture gallery, and all images in the user picture gallery are marked with an emotion type.

At block 304, the image is compared with the user emotion model to determine a target emotion picture from the user emotion model that matches with the image.

It should be pointed out that, the user emotion model includes multiple face images, and each face image has been marked with an emotion type. If a matching rate between the image and a first image is greater than a preset threshold (such as 95%), the emotion type corresponding to the first image is the emotion type of the user. The first image is any image in the user emotion model.

At block 305, an emotion type of the user is determined according to the target emotion picture.

At block 306, a type of a picture to be pushed is determined according to the emotion type of the user.

At block 307, a target picture that matches with the type of the picture to be pushed is obtained from a picture gallery.

At block 308, the target picture is pushed to the user.

At block 309, a choosing result of the user is recorded; the user emotion model is updated according to the choosing result of the user.

In the method described in FIG. 3, the image is compared with the user emotion model to determine the target emotion picture from the user emotion model that matches with the image; the emotion type of the user is determined according to the target emotion picture. By analyzing the image containing facial features totally to determine the emotion type of the user and recommending a picture matching with the emotion type of the user, it is convenient for the user to acquire a picture matching the current mood.

Fifth Implementation

Based on the implementations described above, a mobile terminal is provided by the fifth implementation. The mobile terminal provided by this implementation can be used to perform the method described in block 101 to block 105.

Figure 4:
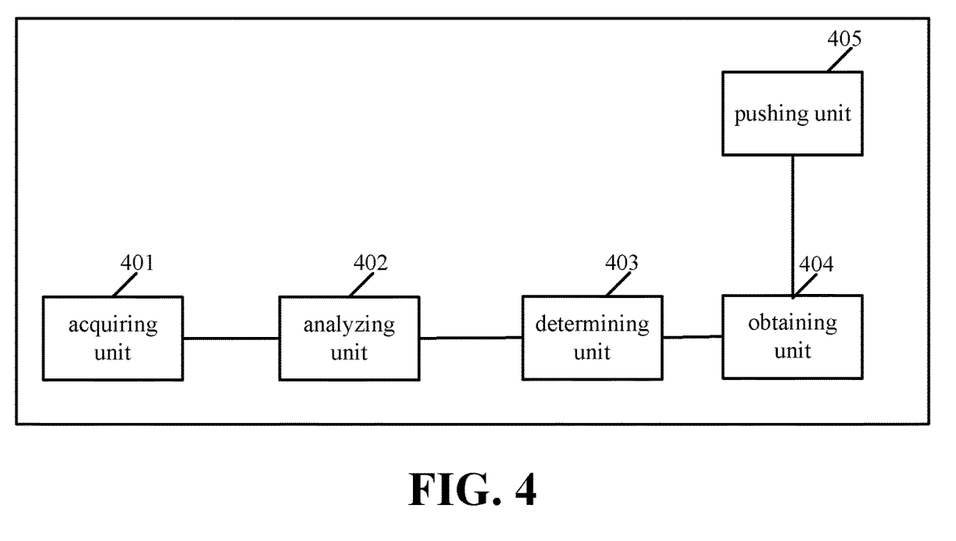
FIG. 4 is a schematic block diagram illustrating a mobile terminal according to an implementation of the present disclosure.

Referring to FIG. 4, FIG. 4 is a schematic block diagram illustrating a mobile terminal according to an implementation of the present disclosure. The mobile terminal described in FIG. 4 can includes an acquiring unit 401 (such as a camera), an analyzing unit 402 (such as a processor), a determining unit 403 (such as a processor), an obtaining unit 404 (such as a processor), and a pushing unit 405 (such as a display screen). And the analyzing unit 402, the determining unit 403, and the obtaining unit 404 can be integrated in one processor.

The acquiring unit 401 is configured to acquire an image containing a facial expression of a user, when a screen is lit. The analyzing unit 402 is configured to analyze the image to determine an emotion type of the user. The determining unit 403 is configured to determine a type of a picture to be pushed according to the emotion type of the user. The obtaining unit 404 is configured to filter a picture gallery to obtain a target picture that matches with the type of the picture to be pushed. The pushing unit 405 is configured to push the target picture to the user.

Sixth Implementation

Based on the implementations described above, another mobile terminal is provided by the sixth implementation. The mobile terminal provided by this implementation can be used to perform the method described in block 201 to block 206.

Figure 5:
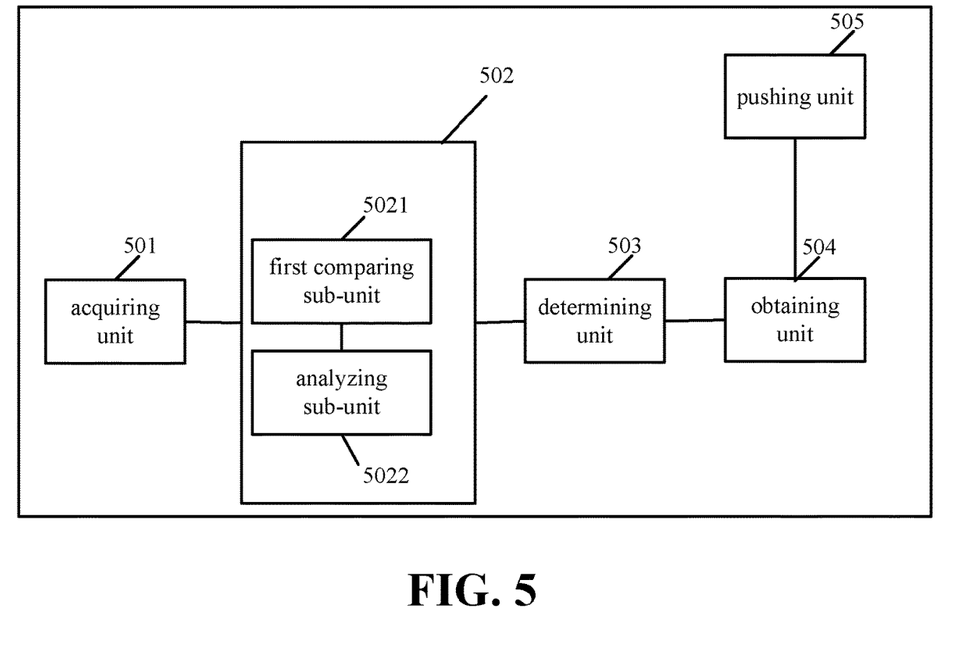
FIG. 5 is a schematic block diagram illustrating another mobile terminal according to an implementation of the present disclosure.

Referring to FIG. 5, FIG. 5 is a schematic block diagram illustrating another mobile terminal according to an implementation of the present disclosure. The mobile terminal shown in FIG. 5 can further include an acquiring unit 501 (such as a camera) and an analyzing unit 502 (such as a processor). The acquiring unit 501 is configured to acquire an image containing a facial expression of a user, when a screen is lit. The analyzing unit 502 is configured to analyze the image to determine an emotion type of the user.

Thereinto, the analyzing unit 502 includes a first comparing sub-unit 5021 (such as a microprocessor core in a multi-core processor) and an analyzing sub-unit 5022 (such as a microprocessor core in a multi-core processor); the first comparing sub-unit 5021 is configured to compare the image with a template to determine a location of eyes and a location of mouth; the analyzing sub-unit 5022 is configured to analyze a shape of the eyes and a shape of the mouth to determine the emotion type of the user.

The mobile terminal can further include a determining unit 503, an obtaining unit 504 (such as a processor), and a pushing unit 505 (such as a display screen). The determining unit 503 is configured to determine a type of a picture to be pushed according to the emotion type of the user. The obtaining unit 504 is configured to filter a picture gallery to obtain a target picture that matches with the type of the picture to be pushed. The pushing unit 505 is configured to push the target picture to the user.

Seventh Implementation

Based on the implementations described above, a mobile terminal is provided by the seventh implementation. The mobile terminal provided by this implementation can be used to perform the method described in block 301 to block 309.

Figure 6:
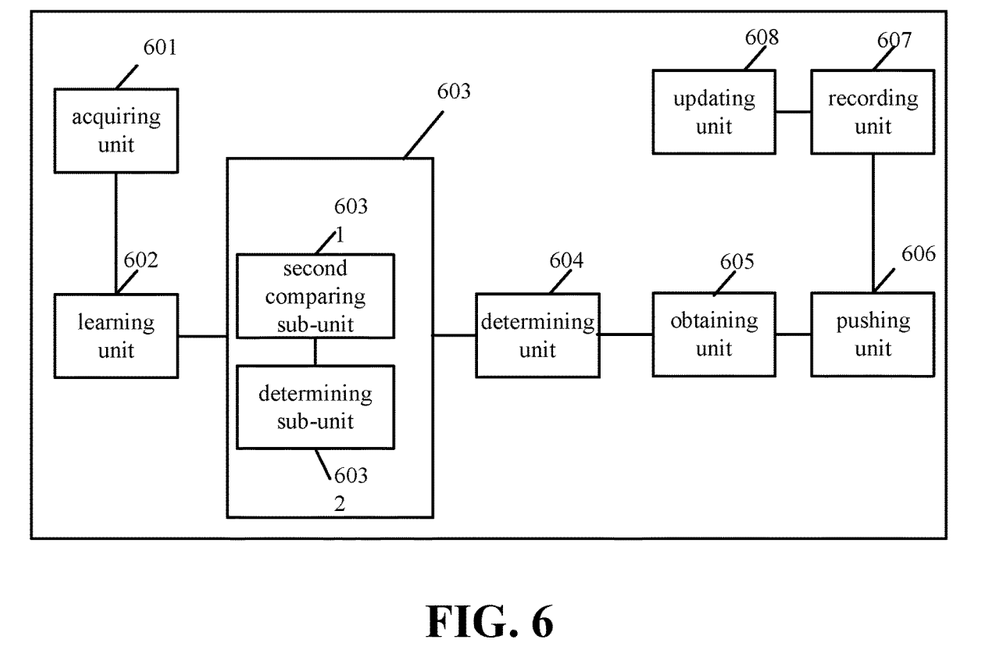
FIG. 6 is a schematic block diagram illustrating another mobile terminal according to an implementation of the present disclosure.

Referring to FIG. 6, FIG. 6 is a schematic block diagram illustrating another mobile terminal according to an implementation of the present disclosure. The mobile terminal shown in FIG. 6 includes an acquiring unit 601 (such as a camera), a learning unit 602 (such as an intelligent microprocessor), and an analyzing unit 603 (such as a multi-core processor). The acquiring unit 601 is configured to acquire an image containing a facial expression of a user, when a screen is lit. The acquiring unit 601 is further configured to acquire a preset number of expression images of the user. The learning unit 602 is configured to learn the expression images according to a preset machine learning scheme to obtain a user emotion model. The analyzing unit 603 is configured to analyze the image to determine an emotion type of the user.

Thereinto, the analyzing unit 603 includes a second comparing sub-unit 6031 (such as a microprocessor core in the multi-core processor) and a determining sub-unit 6032 (such as a microprocessor core in the multi-core processor). The second comparing sub-unit 6031 is configured to compare the image with a user emotion model to determine a target emotion picture from the user emotion model that matches with the image. The determining sub-unit 6032 is configured to determine the emotion type of the user according to the target emotion picture.

The mobile terminal can further include a determining unit 604 (such as a processor), an obtaining unit 605 (such as a processor), a pushing unit 606 (such as a display screen), a recording unit 607 (such as a memory), and an updating unit 608 (such as a processor). The determining unit 604 is configured to determine a type of a picture to be pushed according to the emotion type of the user. The obtaining unit 605 is configured to filter a picture gallery to obtain a target picture that matches with the type of the picture to be pushed. The pushing unit 606 is configured to push the target picture to the user. The recording unit 607 is configured to record a choosing result of the user. The updating unit 608 is configured to update the user emotion model according to the choosing result of the user.

Eighth Implementation

Based on the implementations described above, a mobile terminal is provided by the eighth implementation. The mobile terminal provided by this implementation may include at least one processor and a memory, wherein the processor can invoke program codes stored in the memory to perform a method for pushing a picture, which will be described in detail as follows.

Figure 7:
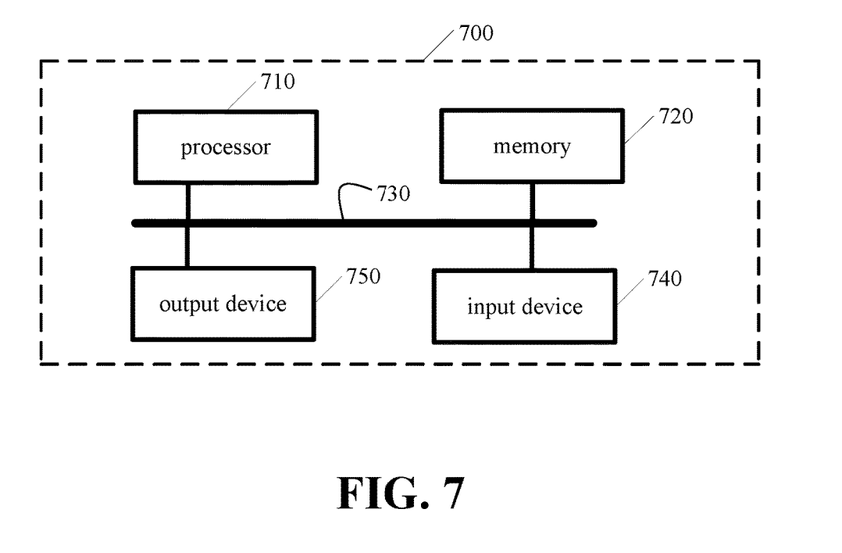
FIG. 7 is a schematic physical structure diagram illustrating a mobile terminal according to an implementation of the present disclosure.

Referring to FIG. 7, FIG. 7 is a schematic structure diagram illustrating a mobile terminal according to an implementation of the present disclosure. As shown in FIG. 7, the mobile terminal can include at least one processor 710 (such as CPU), a memory 720, at least one communication bus 730, an input device 740 (such as a camera, a touchpad, and the like) and an output device 750 (such as a display screen, a speaker, and the like). Thereinto, the communication bus 730 is configured to realize communication connections between these components. The memory 720 can be a high-speed RAM memory or a non-volatile memory, such as at least one disk memory. As an implementation, the memory 720 can be at least one storing device far away from the processor 710. The processor 710 can combine mobile terminals described in FIG. 4 to FIG. 6, a group program codes are stored in the memory 720, and the processor 710 invokes program codes stored in the memory 720 to perform the following operations.

An image containing a facial expression of a user is acquired, when a screen is lit; the image is analyzed to determine an emotion type of the user; a type of a picture to be pushed is determined according to the emotion type of the user; a picture gallery is filtered to obtain a target picture that matches with the type of the picture to be pushed; and the target picture is pushed to the user.

As an implementation, the image is analyzed as follows to determine the emotion type of the user: the image is compared with a template to determine a location of eyes and a location of mouth; and a shape of the eyes and a shape of the mouth are analyzed to determine the emotion type of the user.

As an implementation, the image is analyzed as follows to determine the emotion type of the user: the image is compared with a user emotion model to determine a target emotion picture from the user emotion model that matches with the image; and the emotion type of the user is determined according to the target emotion picture.

As an implementation, before the image is compared with the user emotion model to determine the target emotion picture from the user emotion model that matches with the image, the operation further includes: a preset number of expression images of the user are acquired; the expression images are learned according to a preset machine learning scheme to obtain the user emotion model.

As an implementation, after the target picture is pushed to the user, the operation further includes: a choosing result of the user is recorded; the user emotion model is updated according to the choosing result of the user.

In the implementations of the present disclosure, an image containing a facial expression of a user is acquired, when a screen is lit; the image is analyzed to determine an emotion type of the user; a type of a picture to be pushed is determined according to the emotion type of the user; a picture gallery is filtered to obtain a target picture that matches with the type of the picture to be pushed; and the target picture is pushed to the user. Through the above technical solution, the target picture which matches with the emotion type of the user can be pushed, so as to push a favorite picture of the user more likely and reduce the time for the user choosing the picture.

Ninth Implementation

Based on the implementations described above, a mobile terminal is provided by the ninth implementation. The mobile terminal provided by this implementation may include a general-purpose processor and a memory, wherein the general-purpose processor can invoke program codes stored in the memory to perform a method for pushing a picture, which will be described in detail as follows.

Figure 8:
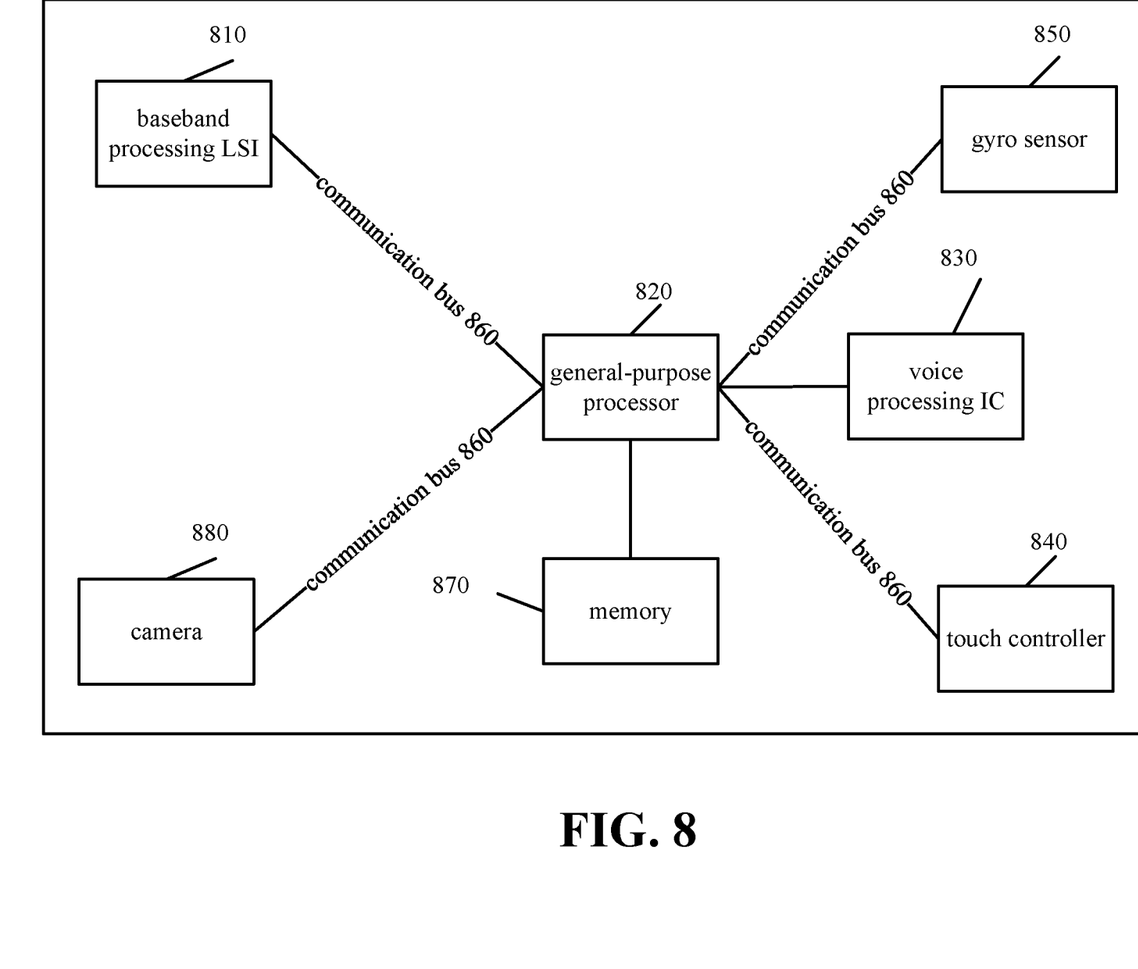
FIG. 8 is a schematic physical structure diagram illustrating another mobile terminal according to an implementation of the present disclosure.

Referring to FIG. 8, FIG. 8 is a schematic structure diagram illustrating another mobile terminal according to an implementation of the present disclosure. As shown in FIG. 8, the mobile terminal can include a baseband processing large scale integrated circuit 810 (baseband processing LSI), a general-purpose processor 820, a voice processing integrated circuit 830 (voice processing IC), a touch controller 840, a gyro sensor 850, a communication bus 860, a memory 870, and a camera 880. Thereinto, the communication bus 860 is configured to realize communication connections between these components. The memory 870 can be a high-speed RAM memory or a non-volatile memory, such as at least one disk memory. The camera 880 is configured to acquire an image containing a facial expression of a user, when a screen is lit. The general-purpose processor 820 can combine mobile terminals described in FIG. 3 to FIG. 6, a group program codes are stored in the memory 870, and the general-purpose processor 820 invokes program codes stored in the memory 870 to perform the following operations.

The image acquired by the camera 880 is analyzed to determine an emotion type of the user; a type of a picture to be pushed is determined according to the emotion type of the user; a picture gallery is filtered to obtain a target picture that matches with the type of the picture to be pushed; and the target picture is pushed to the user.

As an implementation, the image is analyzed to determine the emotion type of the user, which includes the following procedures: the image is compared with a template to determine a location of eyes and a location of mouth; and a shape of the eyes and a shape of the mouth are analyzed to determine the emotion type of the user.

As an implementation, the image is analyzed to determine the emotion type of the user, which includes the following procedures: the image is compared with a user emotion model to determine a target emotion picture from the user emotion model that matches with the image; and the emotion type of the user is determined according to the target emotion picture.

As an implementation, before the image is compared with the user emotion model to determine the target emotion picture from the user emotion model that matches with the image, the operation further includes the following procedures: a preset number of expression images of the user are acquired; the expression images are learned according to a preset machine learning scheme to obtain the user emotion model.

As an implementation, the general-purpose processor includes an application processor and an artificial intelligence (AI) unit, the AI unit is integrated with the application processor, and the AI unit is configured to acquire a preset number of expression images of the user, and learn the expression images according to a preset machine learning scheme to obtain the user emotion model.

Furthermore, the AI unit is further configured to compare the image with the user emotion model to determine the target emotion picture from the user emotion model that matches with the image, and determine the emotion type of the user according to the target emotion picture.

As an implementation, the general-purpose processor includes an application processor and an artificial intelligence (AI) unit, the AI unit is separated from the application processor, and the AI unit is configured to acquire a preset number of expression images of the user, and learn the expression images according to a preset machine learning scheme to obtain the user emotion model.

Furthermore, the AI unit is further configured to compare the image with the user emotion model to determine the target emotion picture from the user emotion model that matches with the image, and determine the emotion type of the user according to the target emotion picture.

The AI unit is a dedicated processing unit for realizing applications of artificial intelligence. The AI unit can perform big data analysis, deep learning, and other artificial intelligent processing, which can improve processing performance of the mobile terminal greatly, and meet more personalized needs of the user. In the aspect of deep learning, the AI unit can acquire a large number of samples to train a neural network model, and perform classification by using the neural network model. For example, the AI unit can be a tensor processing unit (TPU), whose computational performance can reach 180 trillion floating-point operations per second.

It should be pointed out that, a specific form of the AI unit may be hardware and/or software, when the AI unit includes a hardware form, the processor can be integrated with the AI unit, or be separated from the AI unit, which is not limited here.

When the AI unit is integrated with the application processor, if the application processor is a single-core processor, the AI unit can be an intelligent microprocessing circuit in the application processor; if the application processor is a multi-core processor, the AI unit can be an intelligent microprocessor core in the multi-core processor or an intelligent microprocessing circuit in a microprocessor core.

When the AI unit is separated from the application processor, the AI unit can be any co-processor (such as a baseband processor) of an application processor platform architecture other than the application processor; or a new set intelligent microprocessor of the application processor platform architecture other than the application processor; or a new set intelligent processing platform independent of the application processor platform, and the intelligent processing platform includes at least one dedicated intelligent processor, the intelligent processing platform have a communication connection with the application processor platform, optionally, the intelligent processing platform can also have direct communication connections with a memory, a peripheral, etc.

As an implementation, after the target picture is pushed to the user, the method further includes the following procedures: a choosing result of the user is recorded; the user emotion model is updated according to the choosing result of the user.

It will be understood by those of ordinary skill in the art that all or a part of the various methods of the implementations described above may be accomplished by means of a program to instruct associated hardware, the program may be stored in a computer-readable memory, which may include a read-only memory (ROM), a random-access memory (RAM), a programmable read-only memory (PROM), an erasable programmable read only memory (EPROM), a one-time programmable read-only memory (OTPROM), an electrically-erasable programmable read-only memory (EEPROM), a compact disc read-only memory (CD-ROM), or other light disk memory, disk memory, magnetic tape memory, or any other computer-readable media that being configured to bring or store data.

A method for pushing a picture and a mobile terminal disclosed by the implementations of the present disclosure are described in detail above, specific examples are used here to illustrate principles and implementations of the present disclosure, the above description of the implementations is merely used to help understand the method and a core idea of the present disclosure; Meanwhile, to those of ordinary skill in the art, according to the idea of the present disclosure, specific implementations and applied ranges will be changed, in summary, contents of the specification should not be construed as a limitation to the present disclosure.

What is claimed is:

1. A method for pushing a picture, comprising:
   acquiring an image containing a facial expression of a user when a screen is lit;
   comparing the image with a template to determine locations of multiple facial features;
   analyzing shapes of the facial features to determine multiple candidate emotion types;
   determining an emotion type with the highest proportion among the candidate emotion types as the emotion type of the user; and
   pushing a target picture according to the emotion type of the user.

2. The method of claim 1, wherein the pushing the target picture according to the emotion type of the user comprises:
   determining a type of a picture to be pushed according to the emotion type of the user;
   obtaining the target picture that matches with the type of the picture to be pushed from a picture gallery; and
   pushing the target picture to the user.

3. A mobile terminal, comprising:
   a memory configured to store program codes;
   at least one processor coupled with the memory, wherein the program codes, when executed by the at least one processor, are operable with the at least one processor to perform:
     an acquiring unit, configured to acquire an image containing a facial expression of a user when a screen is lit;
     an analyzing unit, configured to analyze the image to determine an emotion type of the user;
     a determining unit, configured to determine a type of a picture to be pushed according to the emotion type of the user;
     a learning unit, configured to learn the expression images according to a preset machine learning scheme to obtain the user emotion model;
     an obtaining unit, configured to obtain a target picture that matches with the type of the picture to be pushed from a picture gallery; and
     a pushing unit, configured to push the target picture to the user;
   wherein the analyzing unit comprises:
     a second comparing sub-unit, configured to compare the image with a user emotion model to determine a target emotion picture from the user emotion model that matches with the image; and
     a determining sub-unit, configured to determine the emotion type of the user according to the target emotion picture;
   wherein the acquiring unit being configured to acquire a preset number of expression images of the user.

4. The mobile terminal of claim 3, wherein the program codes, when executed by the at least one processor, are operable with the at least one processor to perform:
   a recording unit, configured to record a choosing result of the user; and
   an updating unit, configured to update the user emotion model according to the choosing result of the user.

5. A mobile terminal, comprising;
   a camera, configured to acquire an image containing a facial expression of a user when a screen is lit; and
   a general-purpose processor, configured to:
     analyze the image to determine an emotion type of the user;
     determine a type of a picture to be pushed according to the emotion type of the user;
     obtain a target picture that matches with the type of the picture to be pushed from a picture gallery; and
     push the target picture to the user;
   wherein the general-purpose processor configured to analyze the image to determine an emotion type of the user is further configured to:
     compare the image with a user emotion model to determine a target emotion picture from the user emotion model that matches with the image; and
     determine the emotion type of the user according to the target emotion picture;
   wherein the general-purpose processor is further configured to:
     acquire a preset number of expression images of the user; and
     learn the expression images according to a preset machine learning scheme to obtain the user emotion model.

6. The mobile terminal of claim 5, wherein the general-purpose processor comprises an application processor and an artificial intelligence (AI) unit, the AI unit is integrated with the application processor, and the AI unit is configured to:
   acquire a preset number of expression images of the user; and
   learn the expression images according to a preset machine learning scheme to obtain the user emotion model.

7. The mobile terminal of claim 6, wherein the AI unit is further configured to:
   compare the image with the user emotion model to determine the target emotion picture from the user emotion model that matches with the image; and
   determine the emotion type of the user according to the target emotion picture.

8. The mobile terminal of claim 5, wherein the general-purpose processor comprises an application processor and an artificial intelligence (AI) unit, the AI unit is separated from the application processor, and the AI unit is configured to:
   acquire a preset number of expression images of the user; and
   learn the expression images according to a preset machine learning scheme to obtain the user emotion model.

* * * * *